United States Patent [19]

vonReis et al.

[11] 4,362,047
[45] Dec. 7, 1982

[54] FILTER DEVICE FOR CIGARETTE TESTING

[75] Inventors: Charles E. vonReis, Ann Arbor; Attila Vadnay, Saline; Robert E. Corbett, Ann Arbor, all of Mich.

[73] Assignee: Gelman Sciences Inc., Ann Arbor, Mich.

[21] Appl. No.: 237,239

[22] Filed: Feb. 23, 1981

[51] Int. Cl.³ ............................................. G01N 1/22
[52] U.S. Cl. .......................................... 73/28; 55/503
[58] Field of Search ........... 73/28, 23, 863.22, 863.23; 55/503, 270; 210/445

[56] References Cited

U.S. PATENT DOCUMENTS

| 3,686,835 | 8/1972 | Strange et al. | 73/28 |
| 3,748,905 | 7/1973 | Fletcher et al. | 73/28 |
| 3,966,439 | 6/1976 | Vennos | 55/503 |
| 4,148,732 | 4/1979 | Burrow et al. | 55/503 |
| 4,184,360 | 1/1980 | Vadnay et al. | 73/28 |
| 4,256,474 | 3/1981 | Berger, Jr. et al. | 55/503 |

Primary Examiner—Stephen A. Kreitman
Attorney, Agent, or Firm—Reising, Ethington, Barnard, Perry & Brooks

[57] ABSTRACT

The disposable filter device of the invention is particularly suited for testing for the amounts of tars and nicotine in cigarettes and comprises a housing having two components (2,4) one of which has a cylindrical portion (8) and the other of which has an annular flange (48) whereby the two members can be telescoped together with a filter disc (6) therebetween for collecting the tars and nicotine. The member with the cylindrical portion is formed of a relatively soft resilient substantially non-hygroscopic polymer and the member with the annular flange is formed of a relatively hard substantially non-hygroscopic polymer. The resiliency of the member with the cylindrical portion in combination with the relative hardnesses of the members and the particular shapes of the telescoped portions (12,48) enables the two members to be removably secured together with an excellent seal therebetween. Because both members are of substantially non-hygroscopic polymers, the device is substantially free of moisture absorption and hence free of inaccuracies, due to moisture absorption, in determining the amounts of tar and nicotine collected.

6 Claims, 6 Drawing Figures

4,362,047

FILTER DEVICE FOR CIGARETTE TESTING

TECHNICAL FIELD

The subject matter of the present invention is an improved filtering device particularly for testing cigarettes to determine the tar and nicotine content thereof and the effectiveness of filters built into the cigarettes.

BACKGROUND ART

Cigarettes are tested by placing them in a holder and subjecting the oral end to a sub-ambient pressure after lighting the free end. The smoke resulting from this so-called "machine smoke" is passed through a disc shaped filter which is subsequently weighed and analyzed. Previous conventional holding devices for the cigarettes and the disc filters have comprised two conical, individually machined plastic parts which telescope together, the inner part having an outer circumferential groove to receive an O-ring seal which is pressed into the outer part to seal the chamber in which the filter disc is retained between the parts. The machined parts of these previous conventional holding devices are relatively heavy with respect to the filter disc and are made for repeated use. They have a tendency to absorb the products of combustion and thus become discolored. In addition, it has been recognized that the weight may change with use and the change in weight together with the discrepancy in relative weight between the filter and the holder has a tendency to reduce the accuracy of the test results.

U.S. Pat. No. 4,184,360, assigned to the assignee of the present invention, covers a cigarette testing filter assembly formed of light weight inexpensive plastic components. This has a number of advantages, one being that because of the light weight an accurate measurement of the amount of tars and nicotine collected can be made by weighing the entire assembly before and after the tests rather than requiring disassembly and assembly in order to weigh only the filter disc before and after the test. Another advantage is that because of the low cost, the entire assembly can be discarded after only one use thereby saving all the trouble and expense of cleaning between tests, as well as avoiding the testing inaccuracies which frequently result in repeated use despite the intermediate cleaning operations. But whereas the assembly covered by the aforesaid patent does have significant advantages, there are some problems with such an assembly one of which is that of attaining and retaining good seals between the components without requirement for maintaining close tolerances in the manufacture of the components. Also, just as is true of previous cigarette testing filter devices, it was found that at times there were erratic weight readings—weight readings not entirely accounted for by the actual amounts of tar and nicotine collected. It was recognized that with previous cigarette testing filter devices, erratic readings were generally due to small uncontrolled portions of the total amount of tars and nicotine from the cigarette being deposited not on the filter disc which was weighed but on other components which were not weighed. But until the discovery which led to one important aspect of the present invention, the reason for the sometimes erratic weight readings obtained with the assembly of the aforesaid patent remained a mystery.

DISCLOSURE OF INVENTION

Like the assembly of the aforesaid patent, the filter device of the present invention has a housing comprised of two components, one referred to as the main body and the other referred to as the closure cone, which telescope together, with the filter disc clamped therebetween, both of the housing components being formed of organic polymeric material. However, in the device of the present invention the main body is formed of a relatively soft, resilient polymer whereas the closure cone is formed of a relatively hard, rigid organic polymer, and this key feature in combination with the shapes of the portions of these components which telescope together provides a uniformly excellent seal between the components and with the filter disc while yet enabling easy assembly and also easy disassembly should it be desired to remove the filter disc. More specifically, the generally cylindrical telescoping portion of the main body formed of the soft resilient organic polymer has an inner surface with the axially extending portion thereof adjacent the open end of the main body being flared radially outwardly and an axially extending portion of the inner surface adjacent the closure wall of the main body being tapered radially inwardly in the direction of the open end. The telescoping portion of the closure cone, which is formed of a hard rigid organic polymer, is a generally axially extending annular flange the length and diameter and shape of which are such that it fits snugly and sealingly into and against the inner surface of the telescoping portion of the main body and against the filter disc between the main body and the closure cone. The inherent resiliency of the polymer of which the main body is formed, in combination with the aforesaid structure of the telescoping portions, biases the closure cone into snug sealing engagement with the main body and with the filter disc after the closure cone is snap fitted into the main body. Further, in accordance with the invention, the soft resilient organic polymer of which the main body is formed and the hard rigid organic polymer of which the closure cone is formed are both substantially non-hygroscopic, this feature being predicated on the discovery that the erratic weight readings obtained with the previous filter devices were because of erratic moisture pick-up by the previous plastic components—moisture pick-up even from the ambient atmosphere and aside from that derived from the smoke of the cigarette tested.

Hence, the filter device of the present invention affords simple, relatively low cost manufacture and assembly, and disassembly if desired, along with uniformly excellent seals and uniformly accurate weight readings. These and other features and advantages of the invention will appear more clearly from the more detailed description which follows:

BEST MODE FOR CARRYING OUT THE INVENTION

Figure 1:
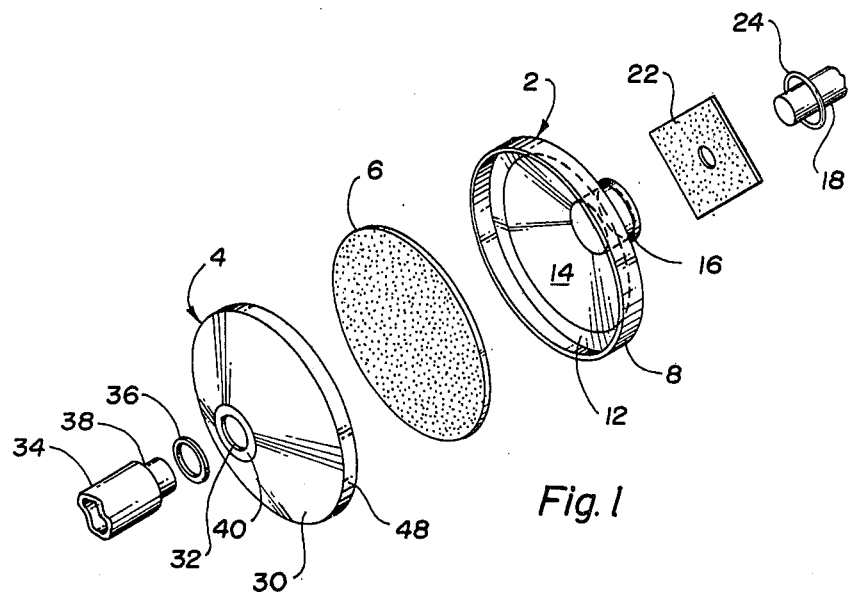
FIG. 1 is an exploded view of the components of the filter device.
Figure 2:
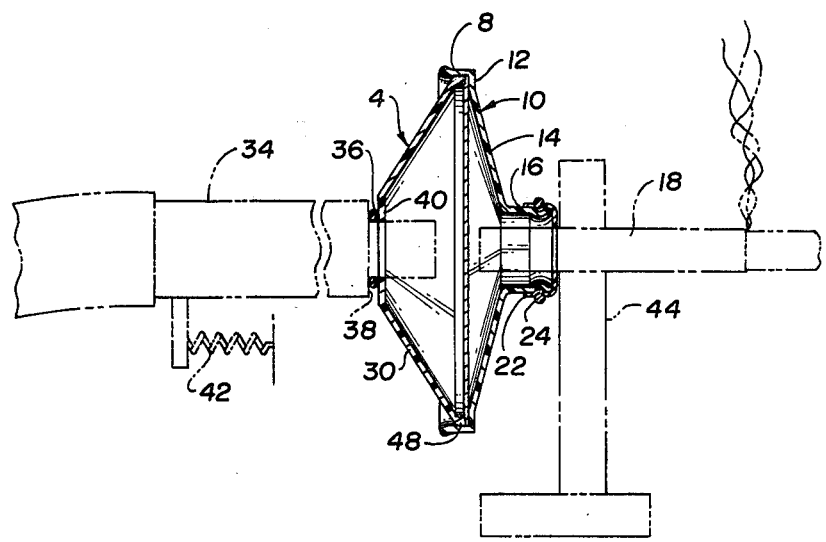
FIG. 2 is a cross-sectional view of the device shown in FIG. 1 after assembly and showing a cigarette being tested and a sub-ambient pressure connection to the device.
Figures 3, 4:
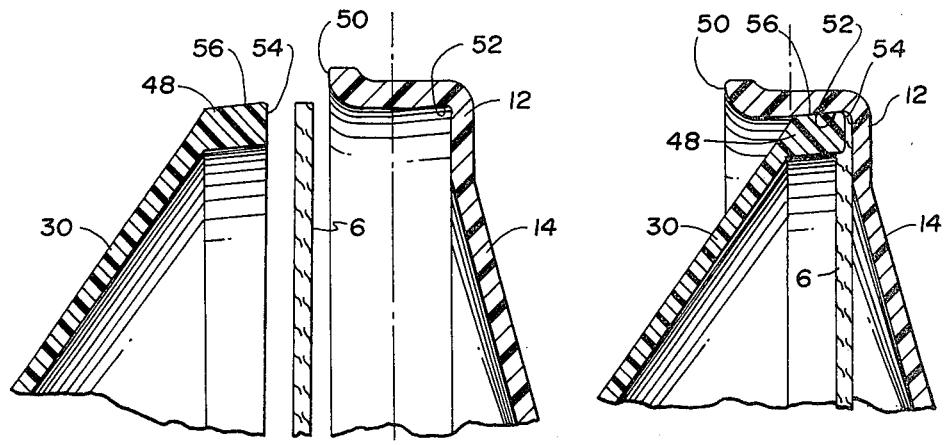
FIG. 3 is a partial cross-sectional view, in enlarged scale, of the device shown in FIG. 2, but prior to assembly.
FIG. 4 is a partial cross-sectional view, in enlarged scale, of the device shown in FIG. 2 after assembly.

Referring now to FIGS. 1, 2 and 3, the filter device comprises a main body 2, closure cone 4 and the filter disc 6. The main body has a generally cylindrical portion 8 which is open at one end and which has, at its other end, a closure wall 10 with a flat radially extending peripheral portion 12, the inner annular surface of which is in a plane normal to the axis of the body, and a conical portion 14 which extends from the peripheral portion to a generally cylindrical nipple 16 which provides the opening for reception of the cigarette 18 being tested. In this embodiment the opening has a diameter larger than that of the cigarette and the cigarette is retained by an elastomeric sheet 22 which is retained on the nipple portion by a rubber band 24 and which has an opening which sealingly receives the cigarette being tested, such cigarette retention means being that conventionally used.

The closure cone 4 has a conical wall portion 30 with an opening 32 at its small-diametered end for sealed connection to a conduit 34 leading to a sub-ambient pressure source, not shown. In this embodiment the sealed connection to the conduit 32 is by means of an elastomeric O-ring 36 which fits around the small-diametered end of the conduit and is biased by conduit shoulder 38 against an annular flat wall portion 40 around the opening in the closure cone, a spring 42 or the like biasing the conduit toward the jig 44 and hence against the closure cone with the O-ring squeezed therebetween—this being the means currently in use for forming a sealed connection to the sub-ambient pressure conduit. At the large-diametered end of the closure cone there is a generally axially extending annular flange 48 which is of importance in its relationship to the generally cylindrical portion and the peripheral wall portion of the main body and hence will be discussed hereinafter, after a more detailed description of the main body portions.

The third component, the filter disc 6, is within the main body extending in a plane transverse to the axis thereof and with its periphery positioned and clamped against the radially extending peripheral wall portion 12 of the main body by the annular flange 48 of the closure cone. The filter disc can and generally will be of the conventional construction and material used for cigarette testing and consisting of a relatively thick compressible mat of glass fibers. It bears mention that whereas such a filter disc has advantage as a smoke or other gas filter in that it can have very small, submicron, pore size while yet allowing a high flow rate, it has a disadvantage in that it renders it difficult to obtain a good seal. That is, even when the periphery of such a filter disc is clamped and compressed between opposed housing surfaces, the compressed periphery cannot be relied upon to afford a good seal of the one housing component to the other since even in its compressed state such a filter disc can be and generally is relatively porous. The present invention solves this problem in that the compressed periphery of the filter disc is not relied upon to provide the seal between the main body 2 and the closure cone 4.

Referring now in particular to FIG. 3, the cylindrical portion of the main body has an inner surface with an axially extending portion 50, adjacent the open end of the main body, which is flared radially outwardly and another axially extending portion 52, between the inner surface portion 50 and the peripheral portion 12 of the closure wall, which is tapered radially inwardly, at an angle of about 5° to the axis of the main body, in the direction of the open end of the main body. Hence, the inner surface of the main body is of relatively large diameter adjacent the open end and adjacent the peripheral portion 12 of the closure wall but with an intermediate portion of relatively small diameter, at the junction of radially inwardly tapered portion 52 and radially outwardly flared portion 50.

Annular flange 48 of the closure cone has a flat end surface 54, which fits against the peripheral portion of the filter disc, and an outer surface 56 which fits against the inner surface portion 52 of the cylindrical portion of the main body, the outer diameter of the flat annular end surface 54 being at least approximately the same as the outer diameter of the inner surface of the peripheral portion 12 of the closure wall of the main body and the axial length of the flange 48 being at least approximately equal to the axial length of the radially inwardly tapered inner wall portion 52 of the main body. The flange 48 is slightly conical, the outer surface 56 being tapered outwardly at an angle of about 5° to the axis of the conical closure, this being the angle of taper of the inner surface portion 52 of the cylindrical portion of the main body against which the surface 52 fits.

The closure cone is formed of a substantially non-hygroscopic relatively hard, rigid organic polymer preferably having a hardness of from about 60 to 90 on the Rockwell M scale (as measured by ASTM D785 test procedure). A preferred polymer is polystyrene of the commercially available grade which has a hardness of about 75 on the Rockwell M scale and which is substantially non-hygroscopic, such polystyrene being available, for example, from the Dow Chemical Company of Midland, Mich.

The main body is formed of a relatively soft resilient substantially non-hygroscopic organic polymer preferably having a hardness of from 70 to 100 on the Rockwell R scale (as measured by ASTM test method D785). A preferred polymer for the main body is polypropylene of a commercially available grade which has a hardness of about 88 on the Rockwell R scale and which is substantially non-hygroscopic, such polypropylene being available, for example, from Hercules Chemical Company of Taunton, Mass.

By the term "substantially non-hygroscopic organic polymer" is meant an organic polymer having moisture absorption of less than 0.1% by weight of the polymer.

Because of the shapes, as described, of the telescoped or mating portions of the main body and the closure cone, the relative hardnesses of the polymers of which they are formed and the resiliency of the polymer of which the main body is formed, the closure cone can be readily inserted into the main body to the position, as shown in FIG. 2, where it is firmly seated therein, with surface 54 of the closure cone pressed tightly against the periphery of the filter disc and with surface 56 of the closure cone fitted tightly and sealingly against the inner wall of the cylindrical portion of the main body. The shape of this inner wall and that of the flange 48, in combination with inherent resiliency of the polymer of which the main body is formed maintains a bias on the closure cone against the filter disc and also assures a good seal between the engaged portions of the main body and closure cone irrespective of minor variations in the dimensions of these components by reason of manufacturing tolerances.

In operation, suction is applied by conduit 34 to cause the smoke from the cigarette being tested to pass through the filter disc 6 which removes all the tar and nicotine, the filter device being weighed before and after such test to determine the amount of tar and nicotine removed. If desired, the filter disc can be removed, for individual weighing or for analysis of the tars and nicotine collected, by withdrawing the closure cone from the main body.

Figures 5, 6:
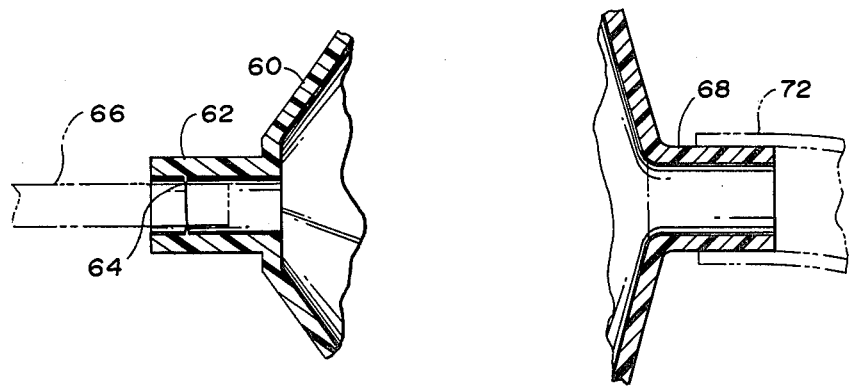
FIG. 5 is a partial cross-sectional view of an embodiment similar to that shown in FIG. 2 but having a modified means for retaining the cigarette being tested.
FIG. 6 is a partial cross-sectional view of an embodiment similar to that of FIG. 2 but having a modified means for connection to the source of sub-ambient pressure.

FIG. 5 shows an embodiment the same as that shown in FIGS. 1-3 except that the main body 60 has a modified nipple portion 62 which eliminates the need for the elastomeric sheet and the rubber band to maintain the cigarette being tested in sealed relationship to the nipple portion. In this embodiment the nipple portion has a thin internal annular flange 64 the inner diameter of which is very slightly less than the diameter of the cigarette 66 being tested, the inherent resiliency and relative softness of the organic polymer of which the main body is formed assuring a sealed fit between the annular flange 64 and the cigarette without significantly pinching the cigarette.

FIG. 6 shown an embodiment the same as already described except that it has a modified means for connection to the suction conduit, such means consisting of a cylindrical portion 68 extending from the closure cone 70 for sealed connection to the conduit 72, the conduit being formed of an elastomeric material which assures a tight sealed fit around and against the cylindrical portion 68. It will be understood that this and other modifications or changes can be made, all within the full and intended scope of the claims which follow, and that whereas the filter device of the invention is especially suited for the testing of cigarettes, other uses, as for the filtration of air, for example are possible.

What is claimed is:
1. A disposable filter device comprising:
(a) a main body having a generally cylindrical portion open at one end thereof and having at the other end thereof a closure wall which has a peripheral portion with an inner annular surface lying in a plane normal to the axis of the body and a portion extending from said peripheral portion to a central, axially-extending nipple, said generally cylindrical portion having an inner wall with a radially outwardly flared portion adjacent said open end and with a portion between said outwardly flared portion and said closure wall which is tapered radially inwardly in a direction toward said open end;
(b) a filter disc in said main body with a peripheral portion positioned against the inner annular surface of said peripheral portion of the closure wall of said main body; and
(c) a closure cone having a conical wall portion with an opening at its small-diametered end for connection to a sub-ambient pressure source and having an annular flange which extends generally axially from the large-diametered end of said conical wall portion of said closure cone and which terminates in an annular surface positioned against the peripheral portion of said filter disc, said annular flange having an outer surface in contact with the radially inwardly tapered portion of the inner wall of the generally cylindrical portion of said main body;
(d) said closure member being formed of a substantially non-hygroscopic organic polymer which is relatively hard and said main body being formed of a substantially non-hygroscopic organic polymer which is relatively soft and resilient whereby the inherent resiliency of the generally cylindrical portion of said main body, in cooperation with the outwardly flared and radially inwardly tapered inner wall portions enables the annular flange of the closure member to be snap fitted into the generally cylindrical portion of the main body and removably retains the annular flange of the closure member within the generally cylindrical portion of the main body in sealed relationship therewith and in pressed contact with the peripheral portion of said filter disc.

2. A filter device as set forth in claim 1 wherein the outer surface of the annular flange of the closure cone has an axial length at least approximately the same as the axial length of the radially inwardly tapered portion of the inner wall of the generally cylindrical portion of the main body.

3. A filter device as set forth in claim 1 wherein the outer surface of the annular flange of said closure cone is tapered outwardly at an angle substantially the same as the angle of taper of the radially inwardly tapered portion of the inner wall of the generally cylindrical portion of the main body.

4. A filter device as set forth in claim 3 wherein the angle of taper of the outer surface of said flange is 5°.

5. A filter device as set forth in claim 1 wherein the organic polymer of which said main body is formed has a hardness of from about 70 to 100 on the Rockwell R scale and the organic polymer of which the closure cone is formed has a hardness of from about 60 to 90 on the Rockwell M scale.

6. A filter device as set forth in claim 1 for the testing of cigarettes and wherein said nipple has an annular portion with an inner diameter slightly less than that of the cigarette to be tested whereby the cigarette to be tested can be inserted into said nipple in sealed relationship to said annular portion.

* * * * *